(12) United States Patent
Thibodeau et al.

(10) Patent No.: US 11,344,321 B2
(45) Date of Patent: May 31, 2022

(54) MULTI-BARREL DRILL GUIDE

(71) Applicant: Conmed Corporation, Utica, NY (US)

(72) Inventors: Robert A. Thibodeau, Saint Petersburg, FL (US); Matthew C. Summitt, Palm Harbor, FL (US); Gregory A. Alfonso, Tampa, FL (US); Robert A. Rofman, Saint Petersburg, FL (US); Erika T. Calvert, Seminole, FL (US); Peter Miller, Largo, FL (US)

(73) Assignee: Conmed Corporation, Utica, NY (US)

( * ) Notice: Subject to any disclaimer, the term of this patent is extended or adjusted under 35 U.S.C. 154(b) by 246 days.

(21) Appl. No.: 16/837,206

(22) Filed: Apr. 1, 2020

(65) Prior Publication Data
US 2020/0222064 A1    Jul. 16, 2020

Related U.S. Application Data

(63) Continuation of application No. 15/679,641, filed on Aug. 17, 2017, now Pat. No. 10,631,884.
(Continued)

(51) Int. Cl.
*A61B 17/17* (2006.01)
*A61B 17/04* (2006.01)
(Continued)

(52) U.S. Cl.
CPC .......... *A61B 17/17* (2013.01); *A61B 17/0482* (2013.01); *A61B 17/1796* (2013.01);
(Continued)

(58) Field of Classification Search
CPC .............. A61B 17/17; A61B 17/1796; A61B 2017/0409; A61B 2017/044; A61B 2017/3449
See application file for complete search history.

(56) References Cited

U.S. PATENT DOCUMENTS 4,744,353 A * 5/1988 McFarland ........ A61B 17/0401
606/96
5,012,818 A   5/1991 Joishy
(Continued)

FOREIGN PATENT DOCUMENTS

| JP | 2009-530004 A | 7/2013 |
| JP | 2014-524787 A | 9/2014 |
| JP | 2013-540501   | 5/2016 |

OTHER PUBLICATIONS

JP Office Action, App. No. 2019-566827, dated Aug. 31, 2021, pp. 1-11.

*Primary Examiner* — Nicholas W Woodall
(74) *Attorney, Agent, or Firm* — Bond, Schoeneck & King, PLLC; Frederick J. M. Price

(57) ABSTRACT

A multi-barrel drill guide with an elongated body extending along a longitudinal axis having a proximal end and a distal end, an elongated distal guide tube attached to and extending from the distal end of the elongated body, and a handle extending from the elongated body between the proximal end and the distal end. The elongated body has a first channel extending from the proximal end to the distal end and a second channel extending from the proximal end to the distal end at an angle relative to the first channel. The first channel and the second channel intersect at a convergence area at the distal end. A drill bit is movable in a slidable manner within the second channel, and a driver loaded with a suture anchor is movable in a slidable manner within the first channel.

7 Claims, 16 Drawing Sheets

Related U.S. Application Data

(60) Provisional application No. 62/515,074, filed on Jun. 5, 2017.

(51) Int. Cl.
*A61B 17/06* (2006.01)
*A61B 17/29* (2006.01)
*A61B 17/90* (2006.01)

(52) U.S. Cl.
CPC ..... *A61B 17/0401* (2013.01); *A61B 17/06123* (2013.01); *A61B 17/90* (2021.08); *A61B 2017/0409* (2013.01); *A61B 2017/2925* (2013.01)

(56) References Cited

U.S. PATENT DOCUMENTS

| | | | |
|---|---|---|---|
| 5,180,388 A | | 1/1993 | DiCarlo |
| 5,250,055 A | | 10/1993 | Moore et al. |
| 5,306,278 A | * | 4/1994 | Dahl ............ A61B 17/17 408/241 G |
| 5,324,295 A | | 6/1994 | Shapiro |
| 5,531,751 A | | 7/1996 | Schultheiss et al. |
| 5,637,112 A | | 6/1997 | Moore et al. |
| 5,741,266 A | * | 4/1998 | Moran .......... A61B 17/1725 606/104 |
| 5,749,889 A | | 5/1998 | Bacich et al. |
| 5,961,530 A | | 10/1999 | Moore et al. |
| 6,379,364 B1 | | 4/2002 | Brace et al. |
| 6,514,258 B1 | | 2/2003 | Brown et al. |
| 6,716,215 B1 | | 4/2004 | David et al. |
| 6,887,244 B1 | | 5/2005 | Walker et al. |
| 6,913,463 B2 | | 7/2005 | Blacklock |
| 7,185,562 B2 | | 3/2007 | Raines, Jr. et al. |
| 7,195,485 B2 | | 3/2007 | Fischer |
| 7,278,852 B2 | | 10/2007 | Fischer |
| 7,441,480 B2 | | 10/2008 | Raines, Jr. et al. |
| 7,503,920 B2 | | 3/2009 | Siegal |
| 7,559,765 B2 | | 7/2009 | Courvoisier |
| 7,604,658 B2 | | 10/2009 | Wilson et al. |
| 7,625,378 B2 | | 12/2009 | Foley |
| 7,762,164 B2 | | 7/2010 | Nino et al. |
| 7,776,047 B2 | | 8/2010 | Fanger et al. |
| 7,833,230 B2 | | 11/2010 | Cerundolo |
| 7,909,829 B2 | | 3/2011 | Patel et al. |
| 7,909,848 B2 | | 3/2011 | Patel et al. |
| 7,935,123 B2 | | 5/2011 | Fanger et al. |
| 7,938,046 B2 | | 5/2011 | Nino et al. |
| 8,113,833 B2 | | 2/2012 | Courvoisier |
| 8,177,787 B2 | | 5/2012 | Walker et al. |
| 8,282,642 B2 | | 10/2012 | McClintock et al. |
| 8,337,499 B2 | | 12/2012 | Sasing et al. |
| 8,357,163 B2 | | 1/2013 | Sidebotham et al. |
| 8,394,107 B2 | | 3/2013 | Fanger et al. |
| 8,403,931 B2 | | 3/2013 | Sidebotham et al. |
| 8,439,947 B2 | | 5/2013 | Howard et al. |
| 8,444,652 B2 | | 5/2013 | Amis et al. |
| 8,449,545 B2 | | 5/2013 | Sidebotham et al. |
| 8,460,297 B2 | | 6/2013 | Watlington et al. |
| 8,518,043 B2 | | 8/2013 | Sidebotham et al. |
| 8,518,044 B2 | | 8/2013 | Sidebotham et al. |
| 8,523,866 B2 | | 9/2013 | Sidebotham et al. |
| 8,535,316 B2 | | 9/2013 | Lewis et al. |
| 8,540,716 B2 | | 9/2013 | Sidebotham et al. |
| 8,556,897 B2 | | 10/2013 | Sidebotham et al. |
| 8,597,301 B2 | | 12/2013 | Mitchell |
| 8,685,068 B2 | | 4/2014 | Sixto et al. |
| 8,911,474 B2 | | 12/2014 | Howard et al. |
| 8,945,135 B2 | * | 2/2015 | Ries .............. A61B 17/1677 606/96 |
| 8,986,354 B2 | | 3/2015 | Walker |
| 9,044,222 B2 | | 6/2015 | Dross |
| 9,162,350 B2 | | 10/2015 | Nino et al. |
| 9,226,744 B2 | | 1/2016 | Pilgeram |
| 9,282,975 B2 | | 3/2016 | Sweeney |
| 9,433,444 B2 | | 9/2016 | Humphreys et al. |
| 9,439,658 B2 | | 9/2016 | Ford et al. |
| 9,463,028 B2 | | 10/2016 | Sidebotham et al. |
| 9,510,841 B2 | | 12/2016 | Sweeney |
| 9,517,075 B2 | | 12/2016 | Sweeney |
| 9,574,952 B2 | | 2/2017 | Schintee |
| 9,700,327 B2 | | 7/2017 | Maxson |
| 9,717,491 B2 | | 8/2017 | Hoeppner |
| 9,757,171 B2 | | 9/2017 | Sixto et al. |
| 9,770,247 B2 | | 9/2017 | Courvoisier |
| 9,782,193 B2 | | 10/2017 | Thistle |
| 9,877,764 B2 | | 1/2018 | Nino et al. |
| 9,925,068 B2 | | 3/2018 | Bays et al. |
| 9,943,948 B2 | | 4/2018 | Nino et al. |
| 9,955,980 B2 | | 5/2018 | Norton et al. |
| 9,962,167 B2 | | 5/2018 | Stephane |
| 10,118,233 B2 | | 11/2018 | Gruhn et al. |
| 10,172,703 B2 | | 1/2019 | Adams et al. |
| 10,206,692 B2 | | 2/2019 | Sanders |
| 10,219,853 B2 | | 3/2019 | Nino et al. |
| 10,342,678 B2 | | 7/2019 | Flores et al. |
| 10,383,640 B2 | | 8/2019 | Houssiere et al. |
| 2002/0165549 A1 | | 11/2002 | Owusu-Akyaw et al. |
| 2005/0015093 A1 | | 1/2005 | Suh et al. |
| 2006/0111723 A1 | | 5/2006 | Chapolini et al. |
| 2008/0086142 A1 | | 4/2008 | Kohm et al. |
| 2009/0030338 A1 | | 1/2009 | Crocker et al. |
| 2009/0075233 A1 | | 3/2009 | Zhang |
| 2010/0137872 A1 | | 6/2010 | Kam et al. |
| 2011/0177473 A1 | | 7/2011 | Darwish et al. |
| 2013/0123809 A1 | | 5/2013 | Murphy et al. |
| 2014/0081281 A1 | | 3/2014 | Felder |
| 2014/0107672 A1 | | 4/2014 | Dross |
| 2015/0196363 A1 | | 7/2015 | Aman et al. |
| 2016/0015379 A1 | | 1/2016 | Keller et al. |
| 2016/0030056 A1 | | 2/2016 | Ahuja et al. |
| 2016/0045206 A9 | | 2/2016 | Stephane |
| 2016/0166350 A1 | | 6/2016 | Burkhardt et al. |

* cited by examiner

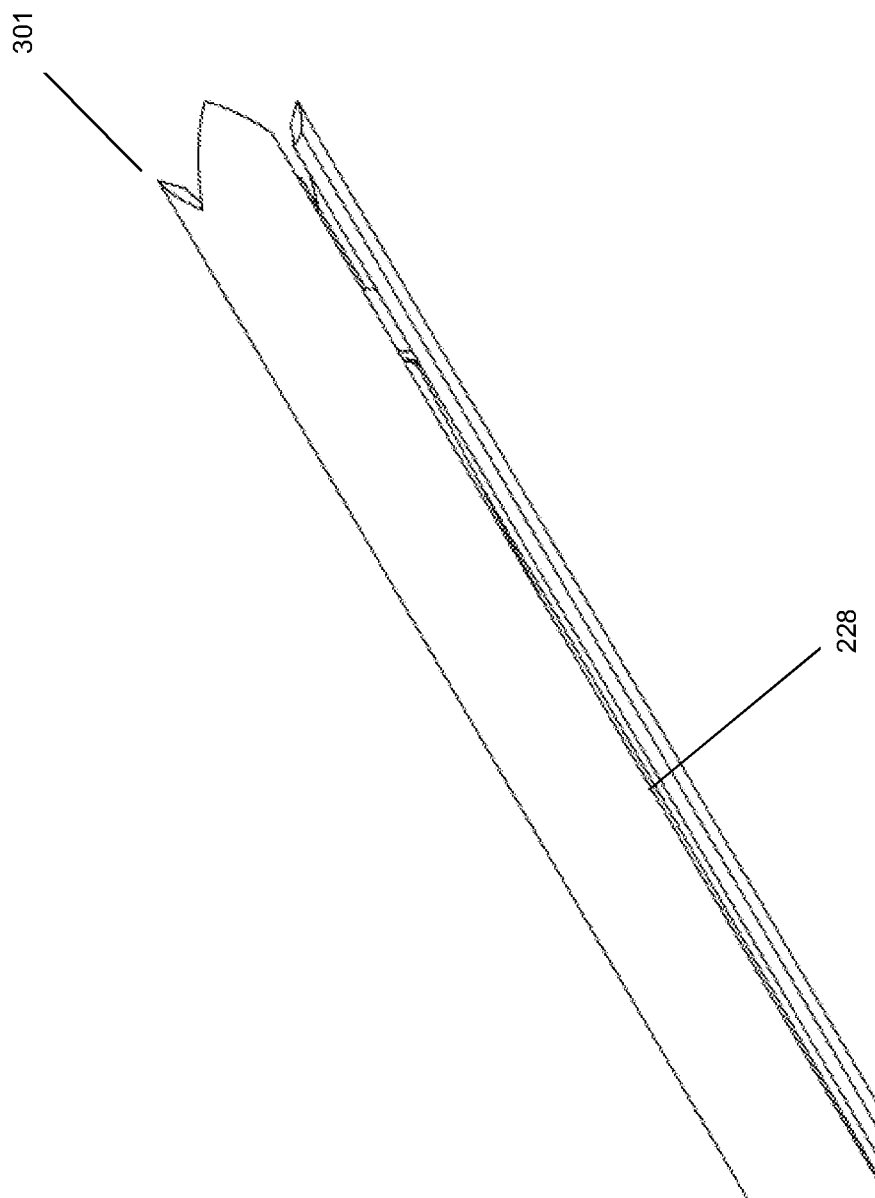

MULTI-BARREL DRILL GUIDE

CROSS-REFERENCE TO RELATED APPLICATIONS

The present application is a continuation of U.S. Non-Provisional application Ser. No. 15/679,641, filed on Aug. 17, 2017, which claims priority to U.S. Provisional Patent Application No. 62/515,074, filed on Jun. 5, 2017.

BACKGROUND OF THE INVENTION

1. Field of the Invention

The present invention relates to a drill guide for drilling a pilot hole at a surgical repair site and inserting a suture anchor in the pilot hole and, more particularly, to a multi-barrel drill guide for both drilling a pilot hole at a surgical repair site and inserting a suture anchor into the pilot hole while maintaining alignment of the drill guide with the pilot hole.

2. Description of the Related Art

Many orthopedic surgical and medical procedures require the fixation of one body to another body. Such bodies may include bone, soft tissue, and prosthetics. One body can be fixed in a position relative to another using connector devices, such as screws and suture anchors (e.g., cannulated knotless suture anchors and soft all suture anchors). For example, various orthopedic surgeries require the insertion and fixation of a suture anchor within a bone. In such surgeries, prior to insertion of a suture anchor, a pilot hole is drilled into the bone. Traditionally, a standard single barrel drill guide is placed at the desired pilot hole location on the bone and a drill is placed through the drill guide to create the pilot hole. The drill is then removed and replaced with a driver pre-loaded with the suture anchor. Thus, a surgeon must completely remove the drill from the drill guide and insert the driver all while maintaining alignment of the drill guide with the pilot hole. Exchanging tools within the drill guide after creation of the pilot hole increases the risk that the alignment of the drill guide with the pilot hole will be lost. A loss of alignment requires additional surgical time to correct the misalignment, if even possible, and may potentially result in trauma to the tissue or bone surrounding the pilot hole. Loss of alignment can also result in the anchor inserter rod bending or the anchor not being able to insert fully into the pilot hole which can add cost as well as surgical time. To avoid misalignment with a standard single barrel guide, an additional assistant may be required to help maintain alignment or attempt realignment.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional single barrel drill guide (as discussed herein and above). For example, removing a drill bit from the drill guide and replacing it with a driver to insert the suture anchor increases the risk of misalignment of the drill guide with the pilot hole, which requires additional surgical time and risks trauma to the surrounding tissue and bone. Therefore, a need exists for a simple to use multi-barrel drill guide that is configured to simultaneously accommodate both a drill bit and a driver with a suture anchor. Such a structural configuration allows for the suture anchor to be in position with the anchor driver in a separate but converging pathway/channel in the drill guide and ready for insertion into a pilot hole immediately after the pilot hole is formed by the drill bit, without having to pull the drill bit out of the drill guide prior to being able to insert the suture anchor driver into the post-convergent area of the drill guide. Various embodiments of the present invention may be advantageous in that they may solve or reduce one or more of the potential problems and/or disadvantages discussed herein.

The present disclosure is directed to an inventive configuration, structure, and resulting function of a multi-barrel drill guide. The multi-barrel drill guide includes an elongated body extending along a longitudinal axis having a proximal end and a distal end with a handle extending from the elongated body at an angle from the longitudinal axis (at an acute angle or orthogonal from the longitudinal axis) at a position between the proximal end and the distal end. The drill guide also includes an elongated distal guide tube attached to and extending from the distal end of the elongated body. In accordance with a preferable embodiment, there is no movable part on an exterior portion or surface of the elongated body. The drill guide has a first channel and a second channel, each of which extends from the proximal end to the distal end. The second channel extends at an angle relative to the first channel. The first channel and the second channel intersect at a convergence area at the distal end. The multi-barrel drill guide is configured to accommodate a suture anchor and driver movable in a slidable manner within the first channel and a drill bit movable in a slidable manner within the second channel, or the drill bit movable in a slidable manner within the first channel and the suture anchor and driver movable in a slidable manner within the second channel. In accordance with preferable embodiment, the elongated body is completely enclosed except for the proximal entrance of the first and second channels, the distal singular exit of the first and second channels post-convergence areas, and an optional slot/slit for a suture connected to the anchor positioned through the outside surface of the elongated body (and preferably into the channel with the driver and suture anchor) and extending from the proximal end of the elongated body (back to the proximal end of the anchor driver) to the distal end of the elongated body (and to the anchor).

According to an another aspect, a method of drilling a pilot hole and inserting a suture anchor in the pilot hole includes, but is not limited to, the steps of: (i) providing a multi-barrel drill guide having an elongated body extending along a longitudinal axis with a proximal end and a distal end, a handle extending from the elongated body at an angle from the longitudinal axis (at an acute angle or orthogonal from the longitudinal axis) at a position between the proximal end and the distal end, an elongated distal guide tube attached to and extending from the distal end of the elongated body, wherein there is no movable part on an exterior portion or surface of the elongated body, a first channel extending from the proximal end to the distal end, a second channel extending from the proximal end to the distal end at an angle relative to the first channel, and a convergence area at the distal end where the first channel and the second channel intersect; (ii) inserting a driver with a suture anchor into the first channel and a drill bit into the second channel; (iii) positioning the distal end of the drill guide against a bone; (iv) extending the drill bit through the convergence area; (v) drilling a pilot hole into the bone with the drill bit; (vi) retracting the drill bit past the convergence area at the distal end of the elongated body of the drill guide; (vii) extending the driver with the suture anchor through the first channel and the convergence area; (viii) implanting the suture anchor into the pilot hole; (ix) pulling a length of suture connected to the suture anchor through a slit positioned through the exterior surface of the elongated body and into the first channel; and (x) removing the drill guide from the bone. The above referenced method can be performed with the drill bit being positioned within the first channel and the driver with the suture anchor being positioned within the second channel.

Suture material or sutures, as the terms are used and described herein an include monofilament or multi-filament suture as well as any other metallic or non-metallic filamentary or wire-like material suitable for performing the function of a suture. This material can include both bioabsorbable and non-absorbable materials.

Suture anchors, as the term is used herein, can include soft suture anchors and rigid suture anchors. Soft suture anchors are formed from filaments of suture material which are retained within pre-formed bone holes by being deformable to increase their diameter to a size greater than that of the bone hole, to thereby reside within the cancellous bone and under the bone cortex. One such suture anchor is disclosed in U.S. Patent Publication No. 2012/0290004 assigned to the assignee hereof and incorporated by reference herein in its entirety. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion. Methods and devices for inserting/deploying such all-suture anchors are known, examples of which are disclosed in U.S. Pat. No. 9,173,652.

As described in U.S. Pat. No. 8,409,252, for example, "non-soft," "hard" or "rigid" suture anchors generally include a "hard" anchor body portion (that may or may not include inner and outer members) and a suture/filament portion. The anchor body of such suture anchors may be formed of a biocompatible and/or bioabsorbable material. These materials may be of such composition that they are reabsorbed by the body, e.g., during the healing process of the bone. Exemplary materials that are suitable for use in the inner and outer members include, but are not limited to, polyetheretherketone ("PEEK"), polylactic acid/beta-tricalcium phosphate ("PLA/Beta-TCP") composites, ultra-high molecular weight polyethylene ("UHMWPE"), as well as other metallic, non-metallic, and polymeric materials.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which:

FIG. 5 is a front/distal view schematic representation of a multi-barrel drill guide according to an embodiment.

DETAILED DESCRIPTION OF THE INVENTION

Figure 1:
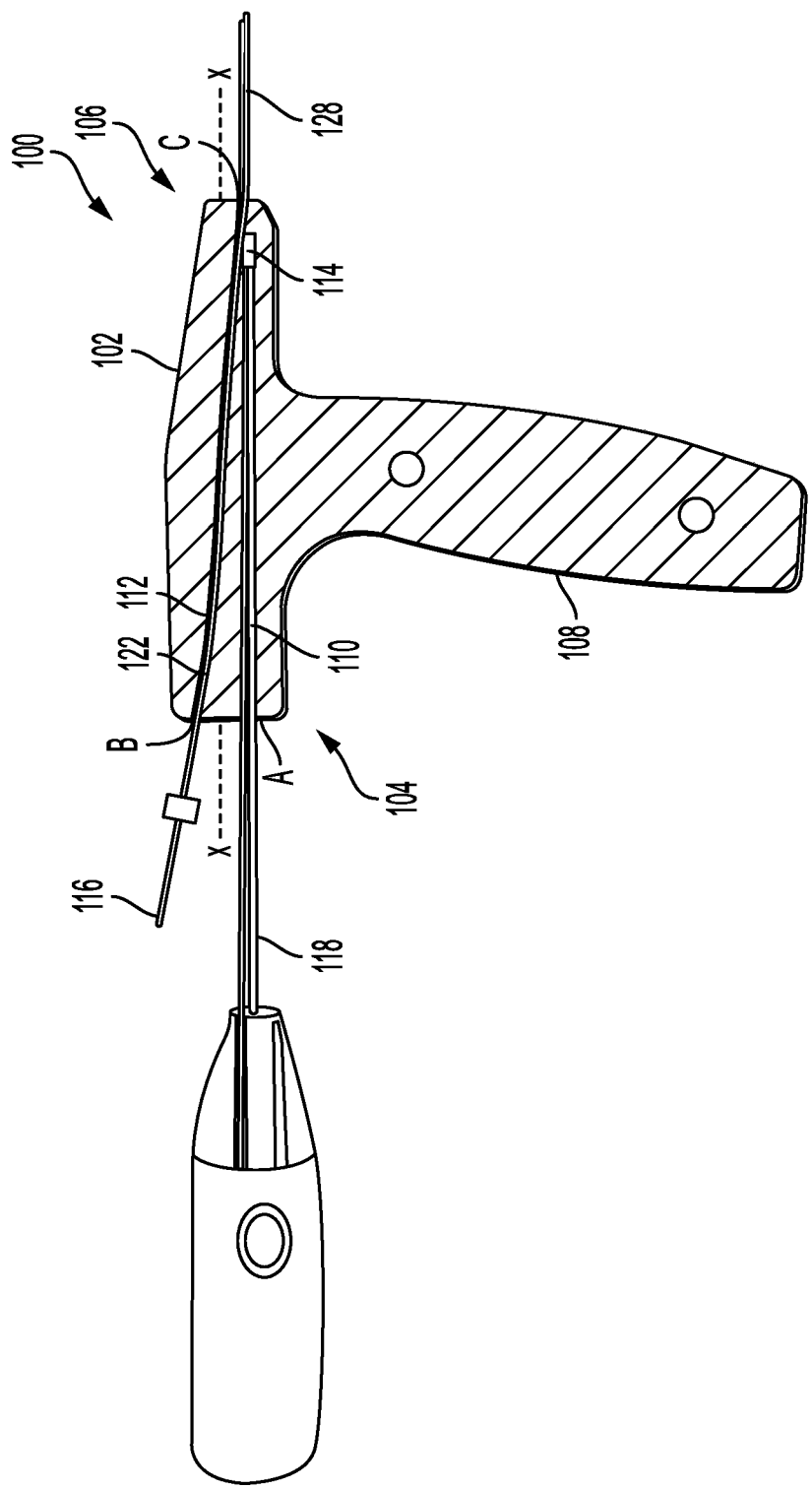
FIG. 1 is a cross-sectional side view schematic representation of a multi-barrel drill guide according to an embodiment.

Referring now to the drawings, wherein like reference numerals refer to like parts throughout, there is seen in FIG. 1 a cross-sectional side view schematic representation of a multi-barrel drill guide 100 according to an embodiment. In the depicted embodiment, the drill guide 100 comprises an elongated body 102 extending along a central longitudinal axis x-x having a proximal end 104 and a distal end 106, a handle 108 extending from the elongated body 102 between the proximal end 104 and a distal end 106, and a distal tube or guide tip 128 extending from the distal end 106. The elongated body 102 has an exterior that is sufficiently enclosed (as described above and shown in the FIGS.). The exterior portion of the elongated body 102 preferably comprises no movable parts that complicate or interfere with easy use of the drill guide 100.

As shown in FIG. 1, the handle 108 extends approximately perpendicular from the elongated body 102 between the proximal end 104 and the distal end 106 to increase balance and control of the drill guide 100. However, the handle 108 may extend at various angles to the central longitudinal axis x-x from any location along the elongated body 102 to provide stability when the user grips the handle 108 to place the drill guide 100 against a desired pilot hole location on a bone.

Still referring to FIG. 1, the elongated body 102 comprises a first channel 110 and a second channel 112 for receiving tools to drill the pilot hole and to insert the suture anchor. In the depicted embodiment, both the first channel 110 and the second channel 112 extend from the proximal end 104 to the distal end 106 of the elongated body 102. As shown in FIG. 1, the first channel 110 and the second channel 112 have different entry points along the proximal end 104 of the elongated body 102. The first channel 110 extends from entry point (A) on the proximal end 104 and the second channel 112 extends from entry point (B) on the proximal end 104. Two separate entry points (A), (B) accommodate two tools—one for drilling the pilot hole and one for inserting the suture anchor into a drilled pilot hole.

In the embodiment illustrated in FIG. 1, the first channel 110 extends approximately straight along a horizontal axis parallel to the central longitudinal axis x-x of the elongated body 102. The second channel 112 extends at an angle relative to the first channel 110 and to the central longitudinal axis x-x, which allows the first channel 110 and the second channel 112 to have separate entry points (A), (B) and one convergence area 114 where the channels converge prior to the single exit point (C) (described below). The separation of the channels 110, 112 permit coexistent placement and storage of two tools within the drill guide 100.

Although the first channel 110 and the second channel 112 extend from different entry points (A), (B) along the proximal end 104 of the elongated body 102, the first channel 110 and the second channel 112 share a single exit point (C) from the elongated body 102 on the distal end 106 of the elongated body 102. This exit point (C) leads to the single distal tube or guide tip 128. As further shown in FIG. 1, the first channel 110 and the second channel 112 extend from the proximal end 104 and converge at a convergence area 114 at the distal end 106 of the elongated body 102. In the depicted embodiment, the convergence area 114 extends from the exit point (C) into the distal end 106. Accordingly, the first channel 110 is separate and distinct from the second channel 112 between the entry points (A), (B) and the convergence area 114. Thus, a user can employ a desired tool (one at a time) in either the first channel 110 or the second channel 112 by extending the tool into the convergence area 114 and out of the drill guide 100 through exit point (C) and into and out of the distal guide tip 128, while the other tool can sit (be positioned and not move) in the opposite channel.

In an additional embodiment, the second channel 112 can include a bent portion 122 which extends at an increased angle relative to the first channel 110. Thus, the bent portion 122 extends at an angle different from the remainder of the second channel 112. The bent portion 122 ensures that there is sufficient distance between entry point (A) and entry point (B) such that insertion and removal of a tool through entry point (A) does not interfere with the positioning of the tool in entry point (B), and vice versa.

For drilling a pilot hole and inserting a suture anchor, the separation of the channels 110, 112 allows for both a drill bit 116 and an anchor driver 118 to be utilized in the drill guide 100 without risking movement that could cause misalignment of the drill guide 100. In one embodiment, a drill bit 116 is placed through the second channel 112 until the drill bit 116 is positioned at exit point (C) and through the distal tube or guide tip 128, while a suture anchor is placed through the first channel 110. In the embodiments shown in FIGS. 1-2, a suture anchor is pre-loaded onto the driver 118 and placed through the first channel 110 up to the convergence area 114, but not extending into the convergence area 114. In an alternative embodiment, the drill bit 116 is placed in the first channel 110, while the driver 118 with the pre-loaded suture anchor is placed within the second channel 112.

Next, the distal guide tip 128 of the drill guide 100 (or distal end 106 of the drill guide 100 if no distal tip 128 is present) is placed against a bone and the drill bit 116 is used to drill the pilot hole (a similar method of use of the drill guide is illustrated and described below with respect to drill guide 200). Thereafter, the drill bit 116 is removed and the driver 118 is extended through the first channel 110, the convergence area 114, and exit point (C) through the distal tip 128 (if present) to insert the suture anchor into the pilot hole. As the first channel 110 and the second channel 112 share common exit point (C) (and common distal tip 128 in some embodiments), the driver 118 can be used to push the suture anchor directly into the pilot hole. Therefore, fewer actions are required by the surgeon to insert the suture anchor after the pilot hole is drilled (i.e., each tool (drill bit; driver with anchor) is present and ready to be used). Thus, there is less risk that the drill guide 100 will be moved in misalignment with the pilot hole.

Figure 2:
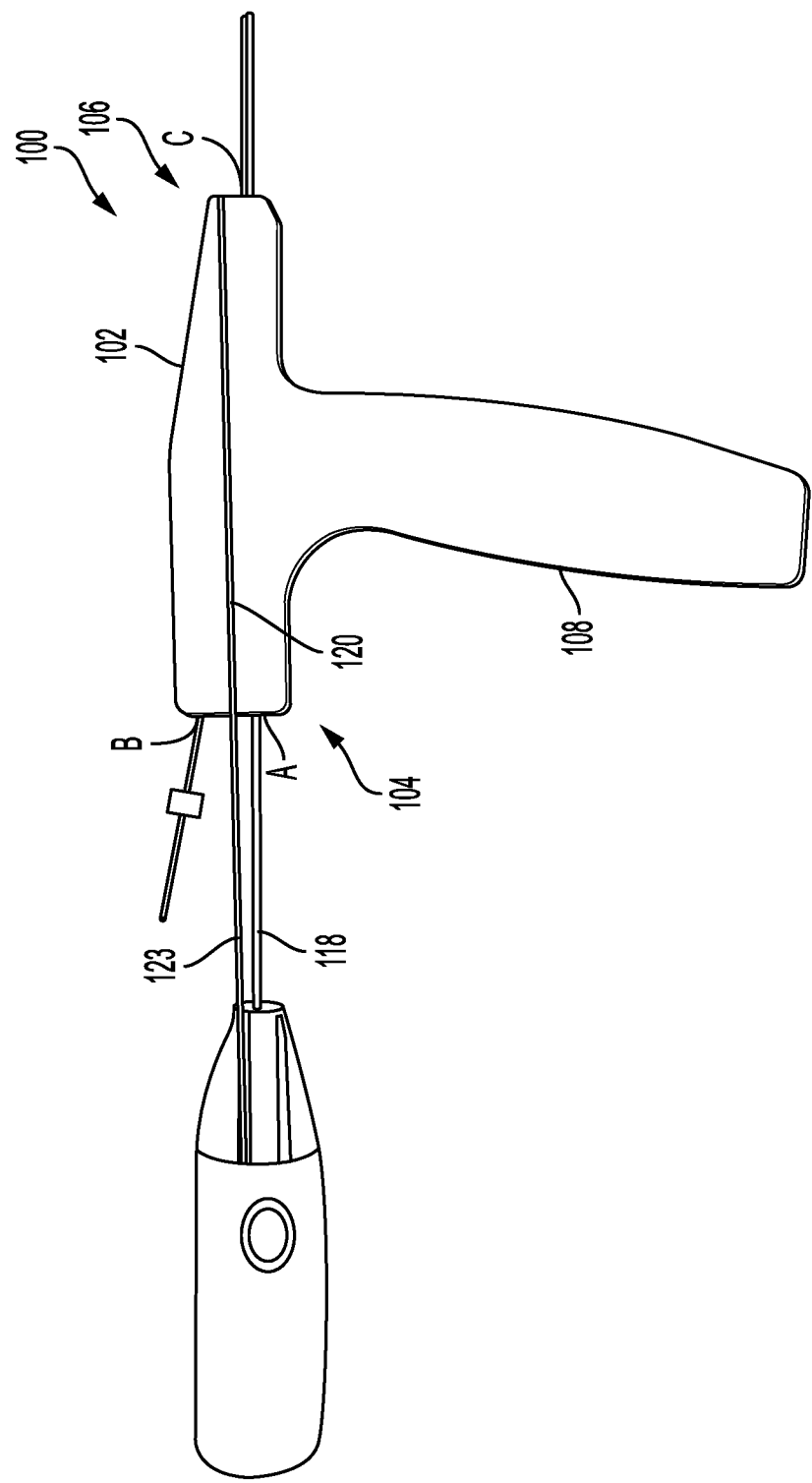
FIG. 2 is an assembled side view schematic representation of a multi-barrel drill guide according to an embodiment.

Referring now to FIG. 2, there is shown a side view schematic representation of a fully assembled multi-barrel drill guide 100 as shown in FIG. 1, according to an embodiment. In the depicted embodiment, the elongated body 102 comprises a slot 120 extending from the proximal end 104 to the distal end 106. The slot 120 can extend through the elongated body 102 into the first channel 110 from a distal portion of the first channel to the distal end 106 of the guide 106, and the proximal portion of the slot 120 does not extend into the first channel so the suture 123 won't interfere with the movement of the driver 118 in the first channel 110 (although, there are embodiments where the suture extends into the first channel along the entire length or between 50 percent and the entire length of the slot). A length of suture 123 extending from the anchor (not shown) can be pulled through the slot 120, so the drill guide 200 can be withdrawn from the pilot hole without disrupting the implanted suture anchor. In addition, the slot 120 facilitates anchors with needles to be used with the drill guide 200. The slot 120 allows needles and suture 123 to be released from the anchor driver handle and pulled away from the guide 100, without requiring the curved suture needles to travel through a channel or slot.

FIGS. 3-13 relate to alternative embodiments of a drill guide 200. Drill guide 200 includes many of the same elements of the drill guide 100, described above. The alternative embodiments include alternate and sometimes additional components, however, some of the alternative embodiments function in a similar manner. Thus, much of the discussion set forth above with respect to previous embodiments with respect to functionality, and the discussion set forth above with respect to some of the basic parts of the drill guide, apply equally to the alternative embodiments discussed below.

Figure 3:
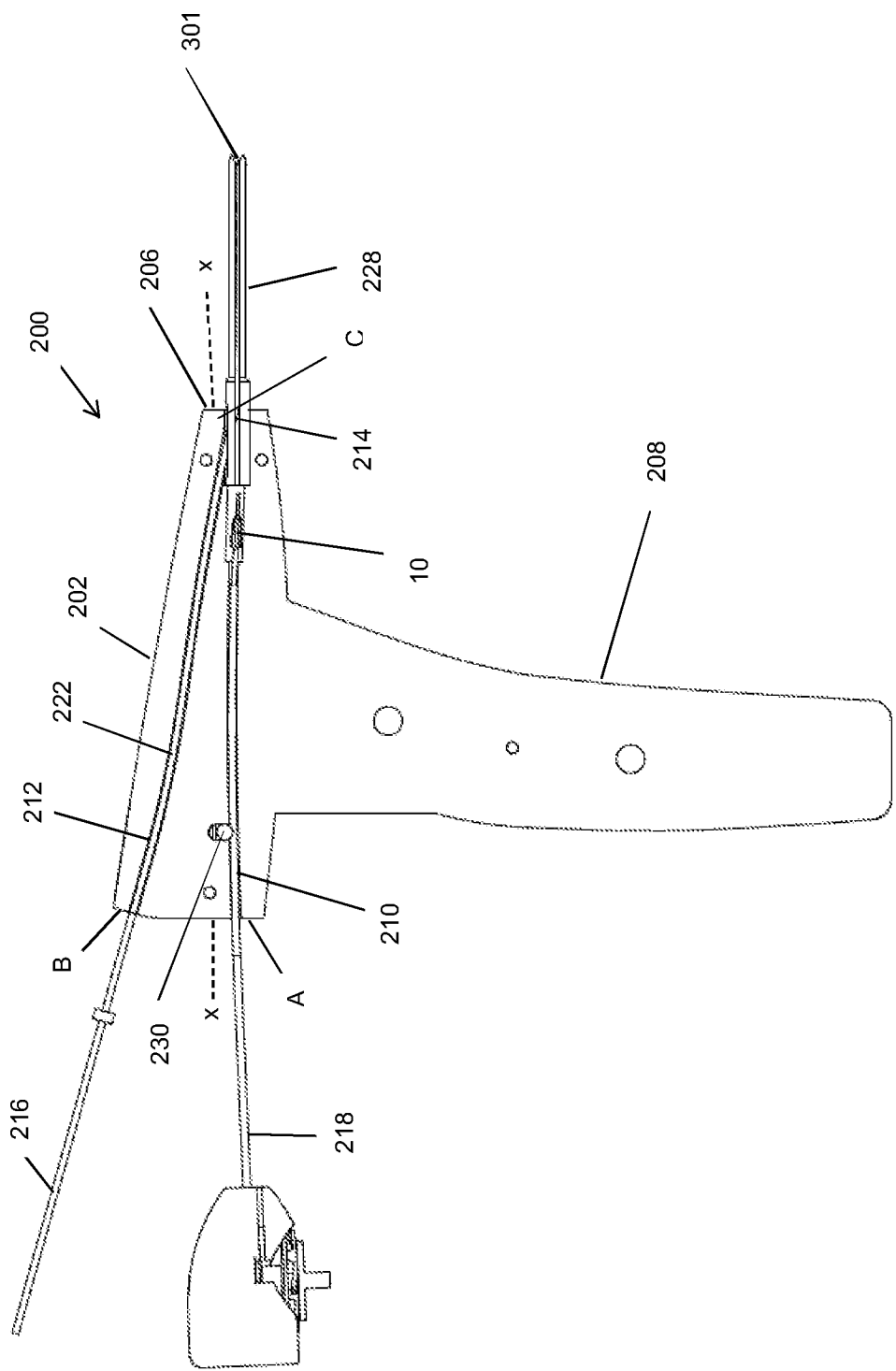
FIG. 3 is a cross-sectional side view schematic representation of a multi-barrel drill guide according to an embodiment.

Turning to FIG. 3, a cross-sectional side view schematic representation of a multi-barrel drill guide 200 according to an embodiment is provided. Similarly to drill guide 100, drill guide 200 comprises an elongated body 202 extending along a central longitudinal axis x-x having a proximal end 204 and a distal end 206, a handle 208 extending from the elongated body 202 between the proximal end 204 and a distal end 206, and a distal tube or guide tip 228 extending distally from the distal end 206. The elongated body 202 has an exterior that is sufficiently enclosed (as described above and shown in the FIGS.). The exterior portion of the elongated body 202 preferably comprises no movable parts that complicate or interfere with easy use of the drill guide 200.

Still referring to FIG. 3, the elongated body 202 comprises a first channel 210 and a second channel 212 for receiving tools to drill the pilot hole and to insert the suture anchor 10. In the depicted embodiment, both the first channel 210 and the second channel 212 extend from the proximal end 204 to the distal end 206 of the elongated body 202. The first channel 210 and the second channel 212 have different entry points along the proximal end 204. The first channel 210 extends from entry point (A) on the proximal end 204 and the second channel 212 extends from entry point (B) on the proximal end 204. Two separate entry points (A), (B) accommodate two tools—one (e.g., a drill bit 216) for drilling the pilot hole and one (e.g., an anchor driver 218) for inserting the suture anchor 10 into a drilled pilot hole.

Figure 7A:
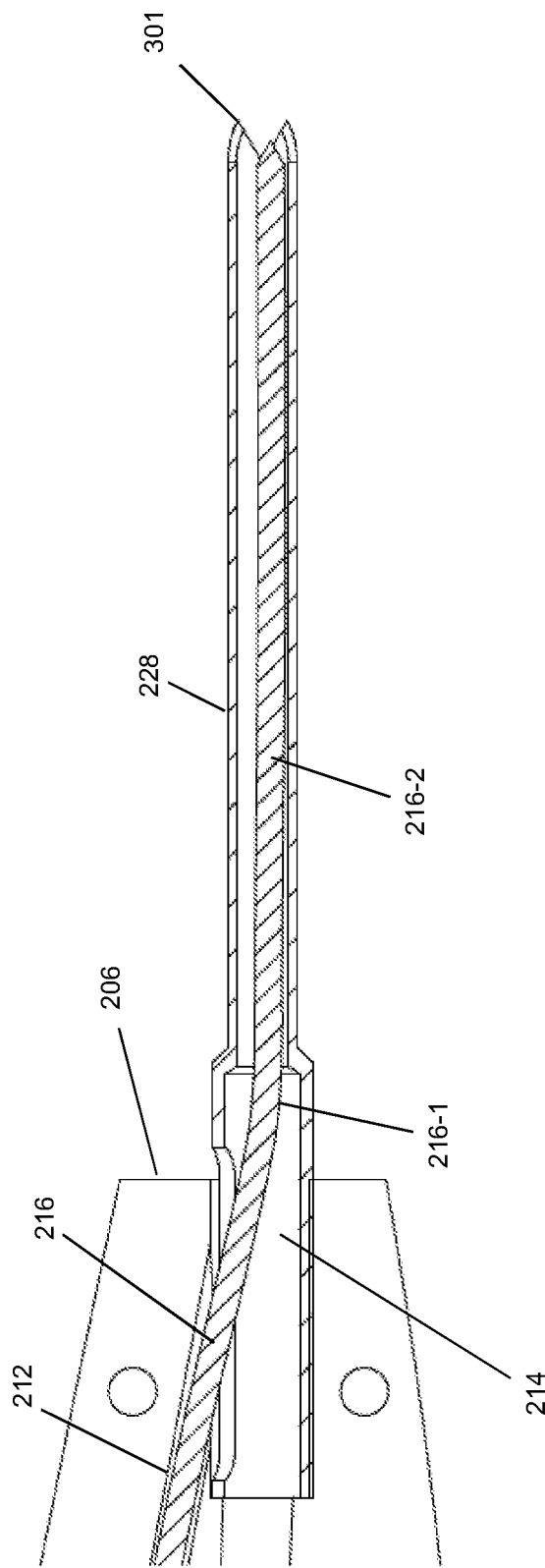
FIG. 7A is a cross-sectional front/distal side view schematic representation of a multi-barrel drill guide according to an embodiment.
Figure 7B:
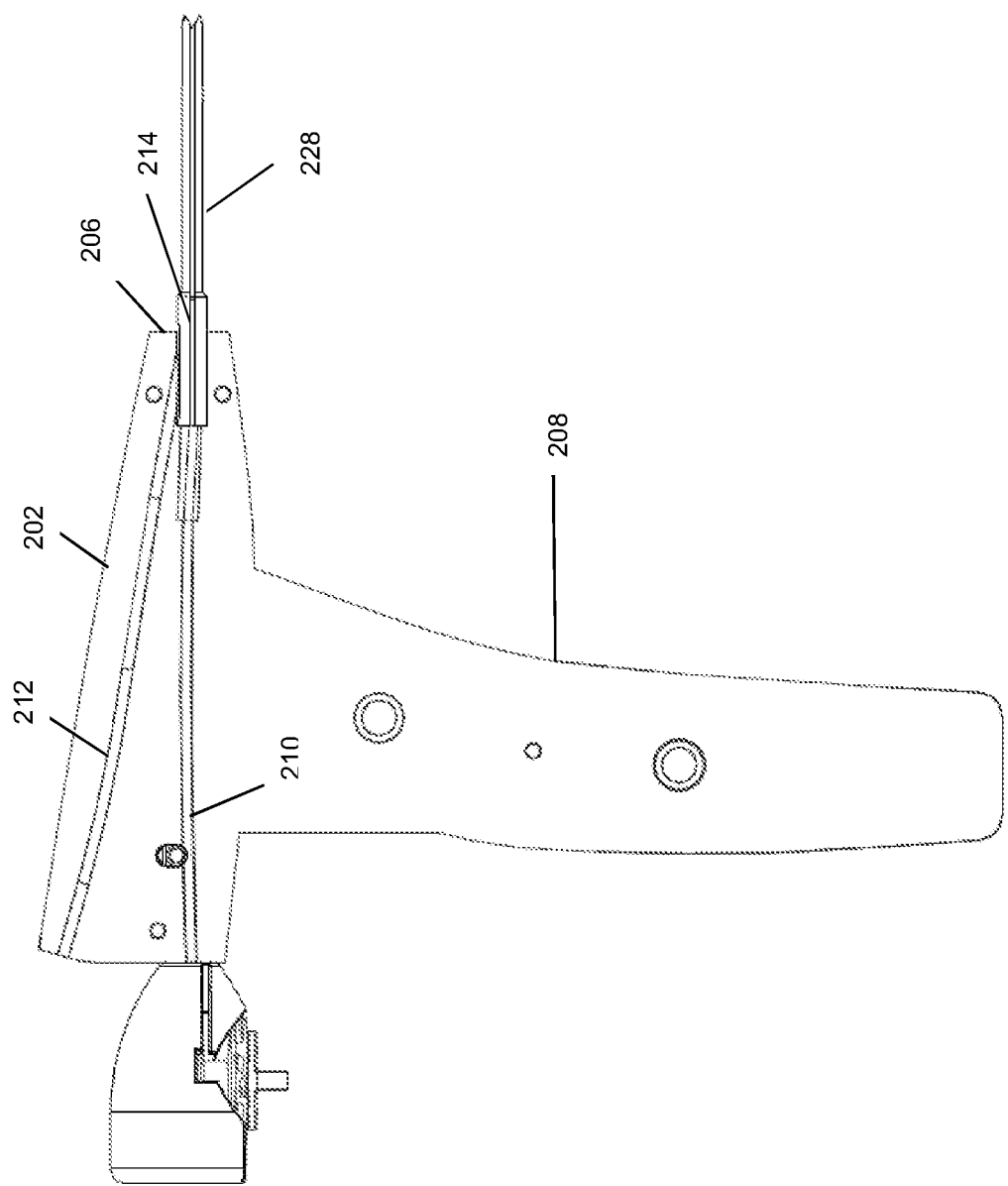
FIG. 7B is a cross-sectional side view schematic representation of a multi-barrel drill guide according to an embodiment.

The first channel 210 extends along the elongated body 202 with a constant, slight curve toward the direction of the handle 208 (discussed further with reference to FIG. 7B). Alternatively, there can be a slight bend toward the direction of the handle, that is not a constant curve, which begins at some point between the proximal and distal ends of the elongated body. The second channel 212 extends at an angle relative to the central longitudinal axis x-x, which allows the first channel 210 and the second channel 212 to have separate entry points (A), (B) and one convergence area 214 where the channels converge prior to the single exit point (C) (described below). The separation of the channels 210, 212 permit coexistent placement and storage of two tools within the drill guide 200.

Although the first channel 210 and the second channel 212 extend from different entry points (A), (B) along the proximal end 204 of the elongated body 202, the first channel 210 and the second channel 212 share a single exit point (C) from the elongated body 202 on the distal end 206 of the elongated body 202. This exit point (C) leads to the single distal tube or guide tip 228. In the depicted embodiment, the convergence area 214 extends from the exit point (C) into the distal end 206. Accordingly, the first channel 210 is separate and distinct from the second channel 212 between the entry points (A), (B) and the convergence area 214. Thus, a user can employ a desired tool (one at a time) in either the first channel 210 or the second channel 212 by extending the tool into the convergence area 214 and out of the drill guide 200 through exit point (C) and into and out of the distal guide tip 228, while the other tool can sit (be positioned and not move) in the opposite channel. The second channel 212 can include a bent portion 222 which extends at an increased angle relative to the first channel 210. Thus, the bent portion 222 extends at an angle different from the remainder of the second channel 212. The bent portion 222 ensures that there is sufficient distance between entry point (A) and entry point (B) such that insertion and removal of a tool through entry point (A) does not interfere with the positioning of the tool in entry point (B), and vice versa.

Figure 4A:
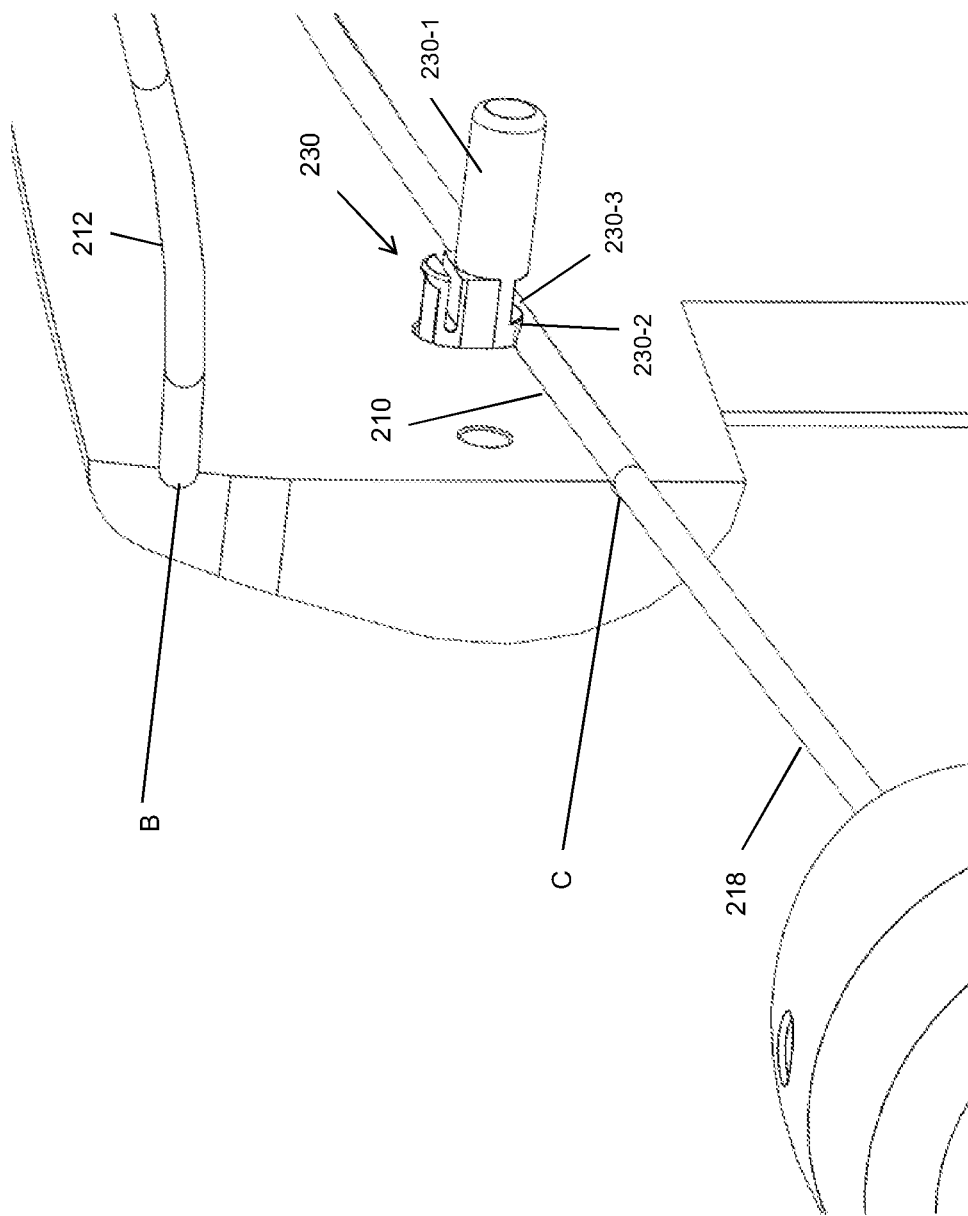
FIG. 4A is a cross-sectional rear view schematic representation of a multi-barrel drill guide according to an embodiment.
Figure 4B:
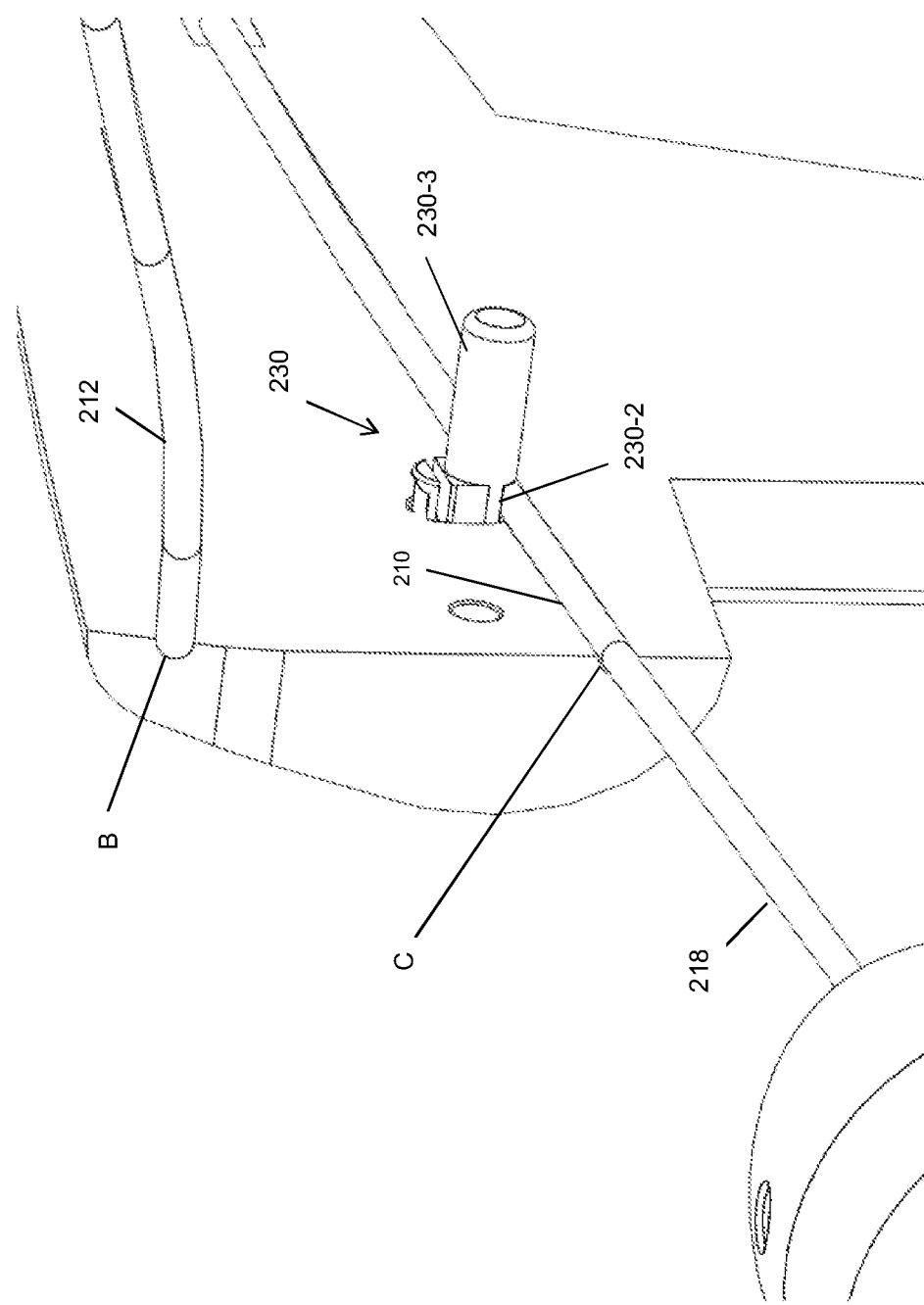
FIG. 4B is a cross-sectional rear/proximal view schematic representation of a multi-barrel drill guide according to an embodiment.

Turning to FIGS. 4A-B, a cross-sectional rear view schematic representation of a multi-barrel drill guide 200 according to an embodiment is provided. A locking mechanism 230 is shown, which includes a locking pin 230-1 with a stop 230-2 and a passageway 230-3. The locking mechanism 230 is actuatable between a locked position—shown in FIG. 4A, and an unlocked position—shown in FIG. 4B. In the locked position, the stop 230-2 contacts the shaft of the anchor driver 218 and holds the anchor driver 218 in place in first channel 210. When the user is ready to use the anchor driver 218 after a pilot hole has been drilled by the drill bit 216, the user can actuate the locking mechanism 230 by pulling on locking pin 230-3 (from the other side of the figures (not shown)), into the page) so that the stop 230-2 no longer contacts the locking pin 230-1, and the shaft of the anchor driver 218 can move freely through passageway 230-3 (as shown in FIG. 4B). Other locking mechanisms are contemplated, as long as the locking mechanism is actuatable from a locked position to an unlocked position (and vice versa) to allow locking and releasing of the anchor driver 218, and can be spring loaded, biased towards the locked or unlocked position (as should be understood by those of skill in the art in conjunction with a review of this disclosure).

As shown in FIG. 5, the distal guide tube 228 can further comprise a plurality of teeth 301 on the distal end 206. The teeth 301 protrude from the distal end of the distal guide tube 228 such that when the drill guide 200 is placed against a bone to create the pilot hole, the teeth 301 grip the bone. Thus, the teeth serve to provide additional stability for the drill guide 200 and are structured to help maintain alignment of the drill guide 200 with the desired pilot hole location on the bone. The teeth can vary in number from one to a plurality, and can be any shape and sharpness that can assist with the above referenced functionality.

Figure 6:
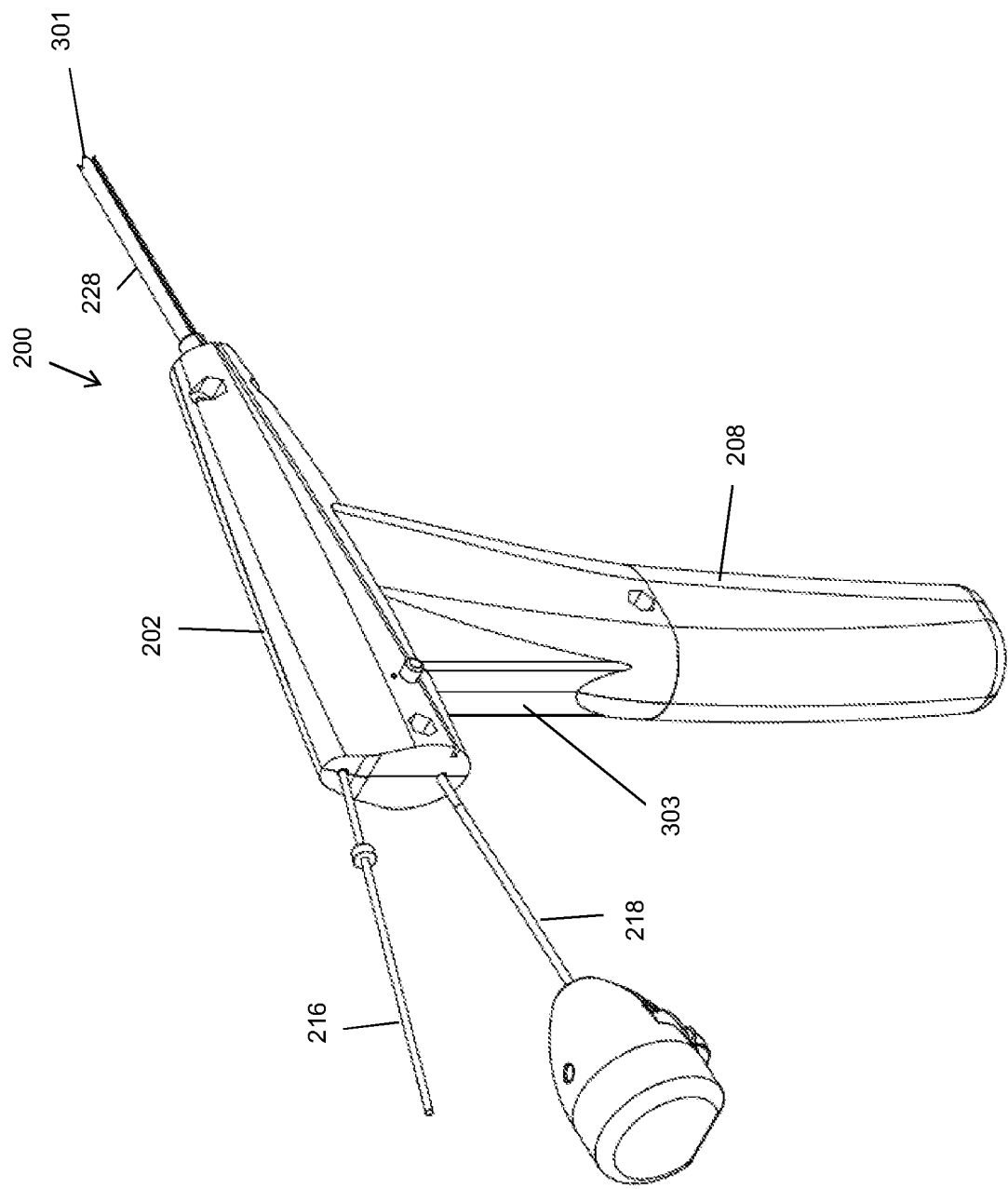
FIG. 6 is an assembled rear perspective schematic representation of a multi-barrel drill guide according to an embodiment.

Turning to FIG. 6, in an additional embodiment, the teeth 301 on the distal end of the distal guide tube 228 may be configured to receive additional force against the bone around a desired location for a pilot hole. In such an embodiment, the handle 208 of the drill guide 200 can further comprise a malleting section 303, which provides additional surface area to the proximal end of the drill guide 200 for striking with a mallet or other similar device. As shown, the malleting section 303 protrudes proximally from the handle 108 near where the handle 208 extends from the elongated body 202 (although, the malleting section 303 can be positioned anywhere near the proximal end of the drill guide 200 and/or handle 208). The malleting section 303 is near the elongated body 302 because striking the malleting section 303 will apply force to the elongated body 202 toward the teeth 301 drive the teeth 301 into the bone around the desired location for a pilot hole. Applying force to the teeth 301 via the malleting section 303 increases the stability of the drill guide 200 against the bone and helps maintain alignment for drilling the pilot hole and inserting the suture anchor.

Turning to FIG. 7A, a cross-sectional side view schematic representation of the distal end of the multi-barrel drill guide 200 according to an embodiment is provided. FIG. 7A shows a part of the drill bit 216 positioned within the second channel 212, through the distal end 206 of the elongated body 202 and within the distal guide tube 228. As shown, the drill bit 216 bends at point 216-1 near convergence area 214, in order to (1) be able to be maneuvered straight through the distal guide tube 228 and (2) to drill a hole in a bone that is substantially parallel and preferably not at an angle to the longitudinal axis x-x. The drill bit 216 is preferably flexible enough to bend as appropriate as it is maneuvered through the convergence area and into the distal guide tube 228, and back out again (similar attributes are contemplated for the anchor driver 218 if it is positioned through the second channel 212 instead). A cylindrical guide sleeve (not shown) can be positioned within the second channel 212, convergence area 214 and/or the distal guide tube 228 that has an inner diameter slightly larger than the diameter of the drill bit 216 and an outer diameter slightly smaller than the diameter of the second channel 212, convergence area 214, and distal guide tube 228. This guide sleeve can position the tip of the drill bit 216 in the center of the distal guide tube 228 to further ensure a particular/predetermined trajectory of the pilot hole.

Figure 7C:
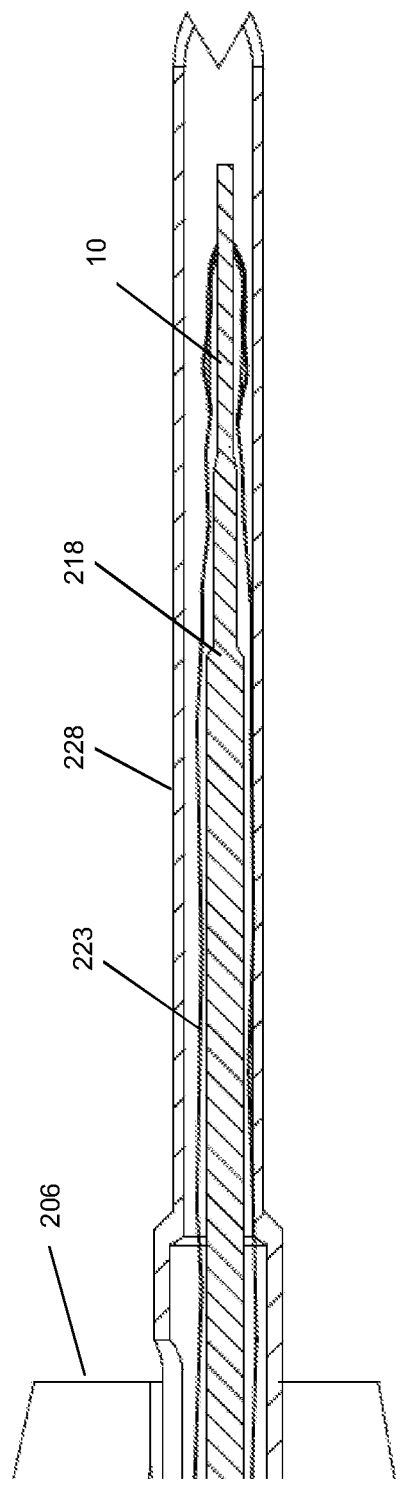
FIG. 7C is a cross-sectional front/distal side view schematic representation of a multi-barrel drill guide according to an embodiment.

Turning to FIG. 7B, a cross-sectional side view schematic representation of the multi-barrel drill guide 200 according to an embodiment is provided. FIG. 7B shows a bend 210-1 in the first channel 210, which is curved in a direction toward the handle 208. As shown, the first channel 210 curves in a direction toward the handle 208 from a point between the proximal end and the distal end of the elongated body 202 to the convergence area 214 (it is contemplated that the curve can begin at any point between the proximal end and the distal end of the elongated body 202 and can extend to the convergence area, just before or just after the convergence area). This bend is structured and configured to position/guide the anchor driver along the same path as the drill bit (substantially straight along the bottom of the distal drill guide 228), so that the anchor can more easily be inserted into the previously drilled bone hole. Stated differently, with this bend 210-1 in place, the anchor is less likely to miss the previously drilled hole, and is more likely to be inserted in the pilot hole without adjusting the distal end of the distal guide tube 228 to sufficiently line up the hole for deployment of the anchor. FIG. 7C is a cross-sectional side view schematic representation of the distal end of the multi-barrel drill guide 200 according to an embodiment. FIG. 7C shows the anchor driver 218 positioned through the distal guide tube 228, and moving along the same path as the drill bit (substantially straight along the bottom of the distal guide tube 228). Accordingly, if the position of the multi-barrel drill guide 200 is maintained with respect to the bone after the pilot hole has been drilled, the anchor 10 with a length of suture 223 should be able to be easily delivered into the previously formed pilot hole without having to move or change the angle the distal guide tube 228 to locate the pilot hole.

Figure 8:
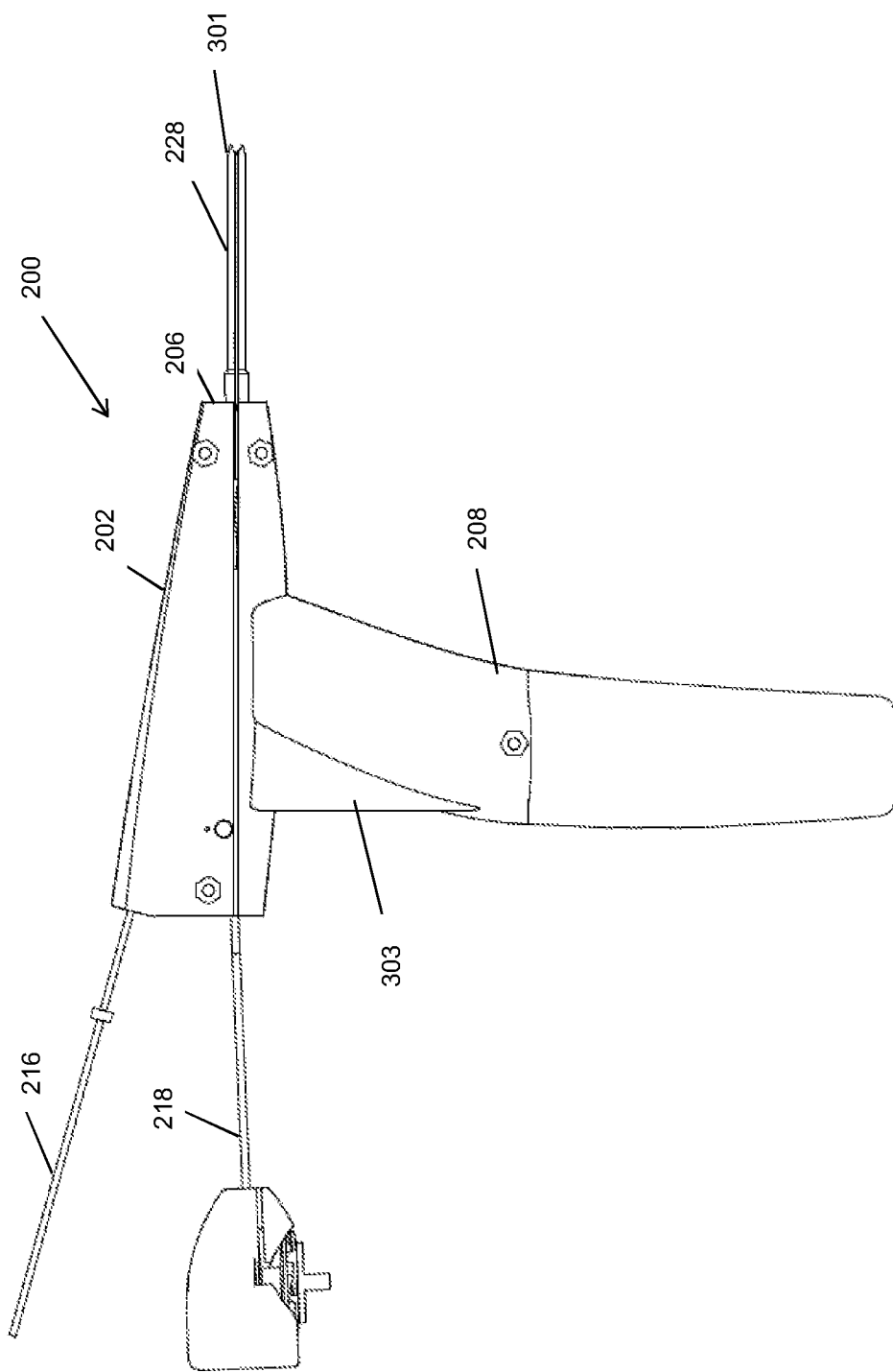
FIG. 8 is an assembled side view schematic representation of a multi-barrel drill guide according to an embodiment.

Turning to FIG. 8, a fully assembled side view schematic representation of a multi-barrel drill guide 200 according to an embodiment is provided. From the proximal end to the distal end of the multi-barrel drill guide 200, FIG. 8 shows the anchor driver 218, drill bit 216, elongated body 202, malleting section 303, handle 208, distal end 206 of the elongated body 202, distal guide tube 228 and teeth 301. The drill bit 216 in this embodiment is preloaded with the distal tip of the drill bit at the distal end of the distal guide tube 228.

FIGS. 9-13 illustrate a method of using the multi-barrel drill guide 200 according to an embodiment. Each of the Figures shows a fully assembled side view schematic representation of a multi-barrel drill guide 200 according to an embodiment.

Figure 9:
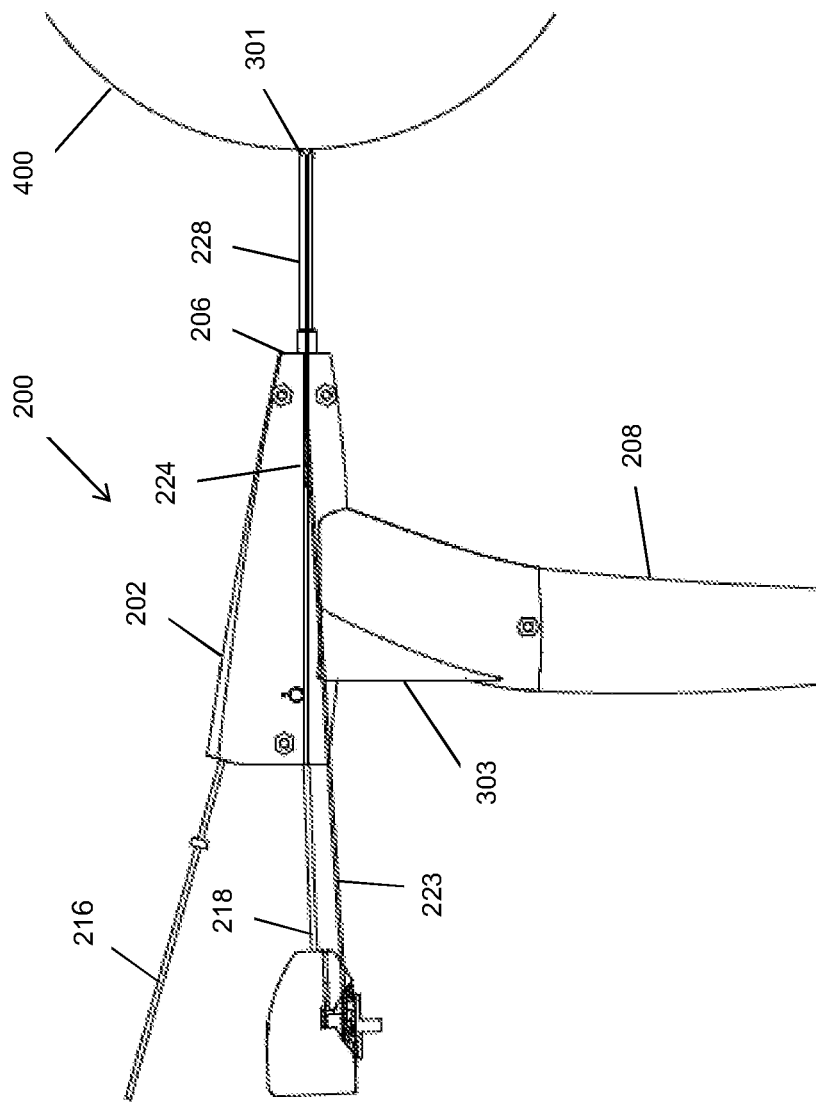
FIG. 9 is an assembled side view schematic representation of a multi-barrel drill guide in use according to an embodiment.
Figure 10:
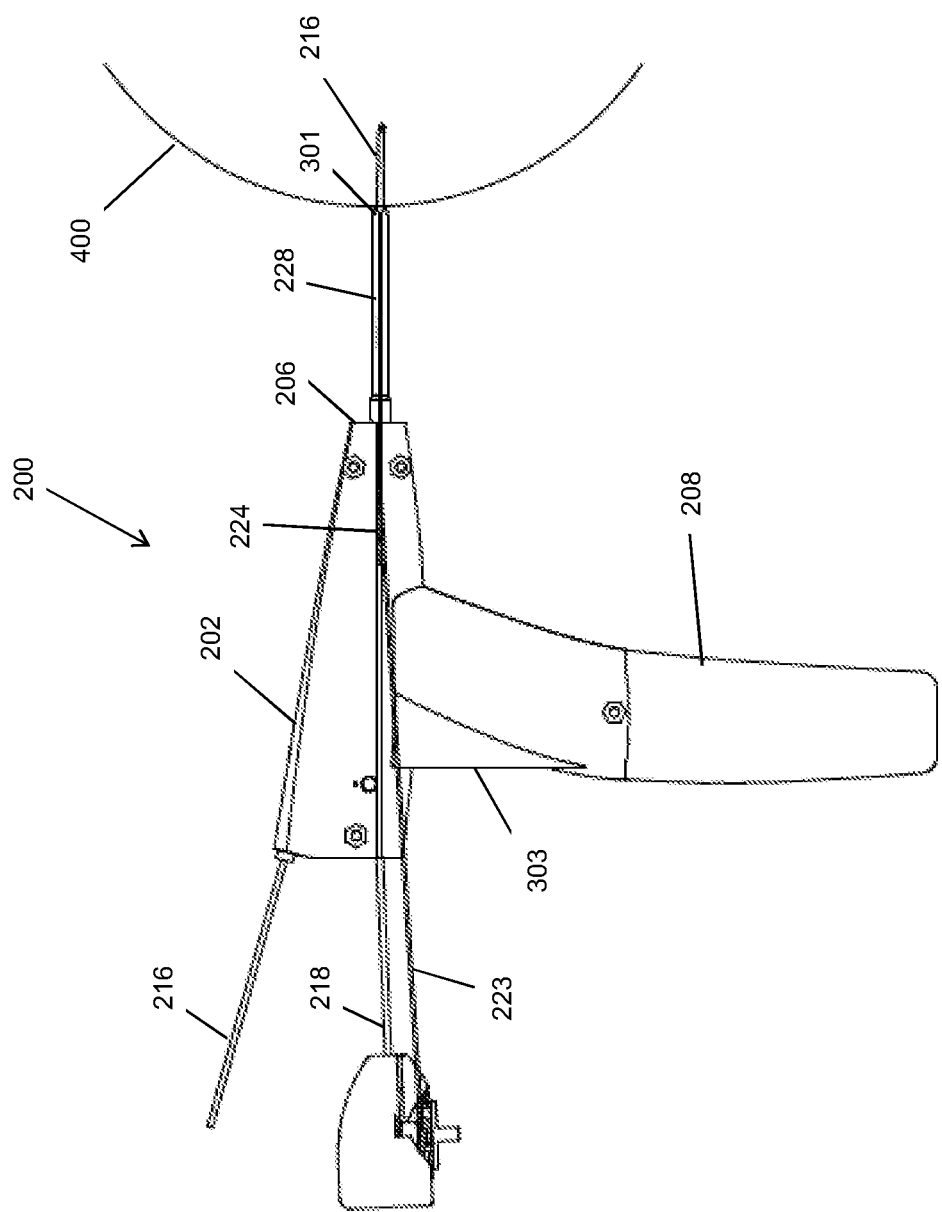
FIG. 10 is an assembled side view schematic representation of a multi-barrel drill guide in use according to an embodiment.
Figure 11:
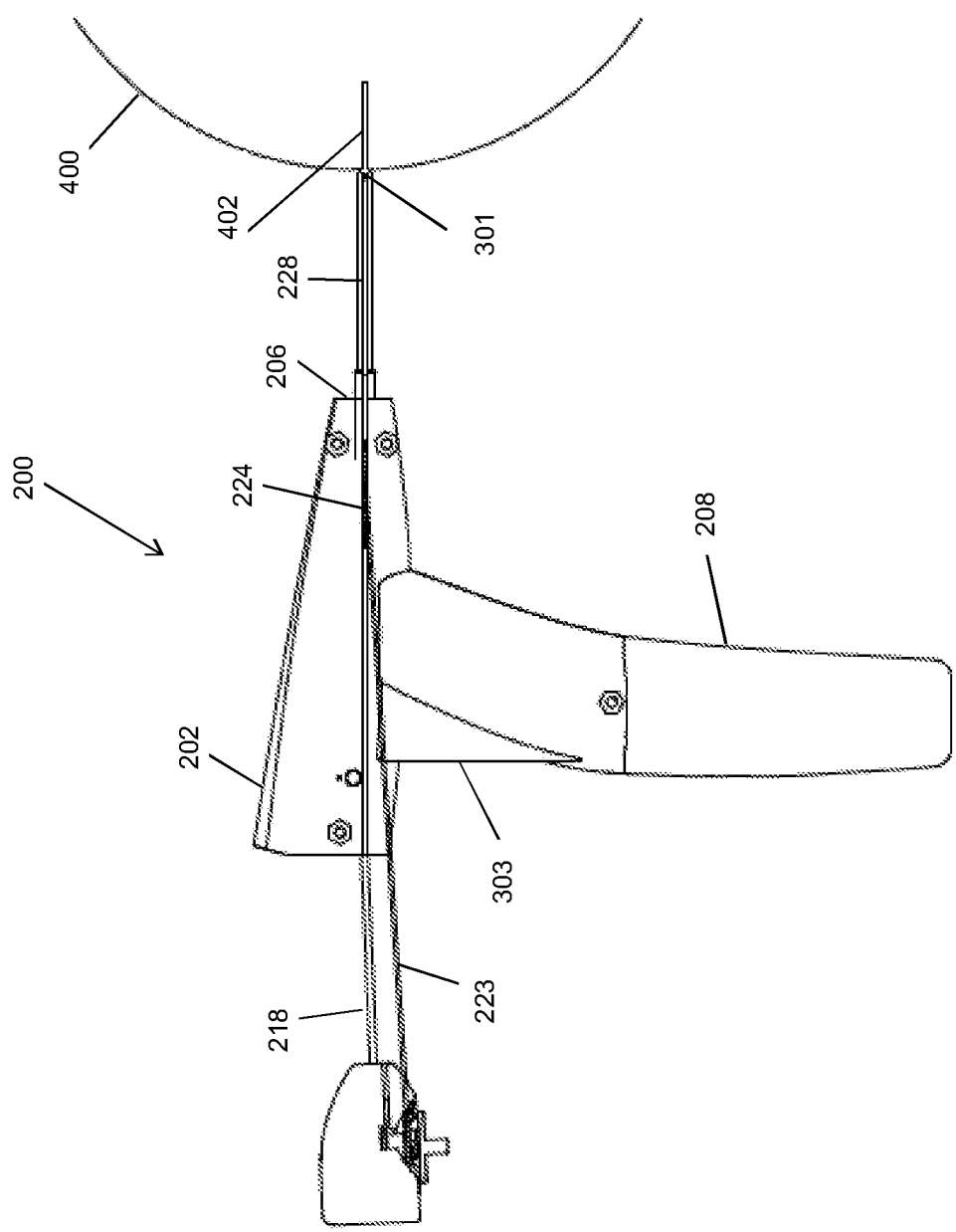
FIG. 11 is an assembled side view schematic representation of a multi-barrel drill guide in use according to an embodiment.
Figure 12:
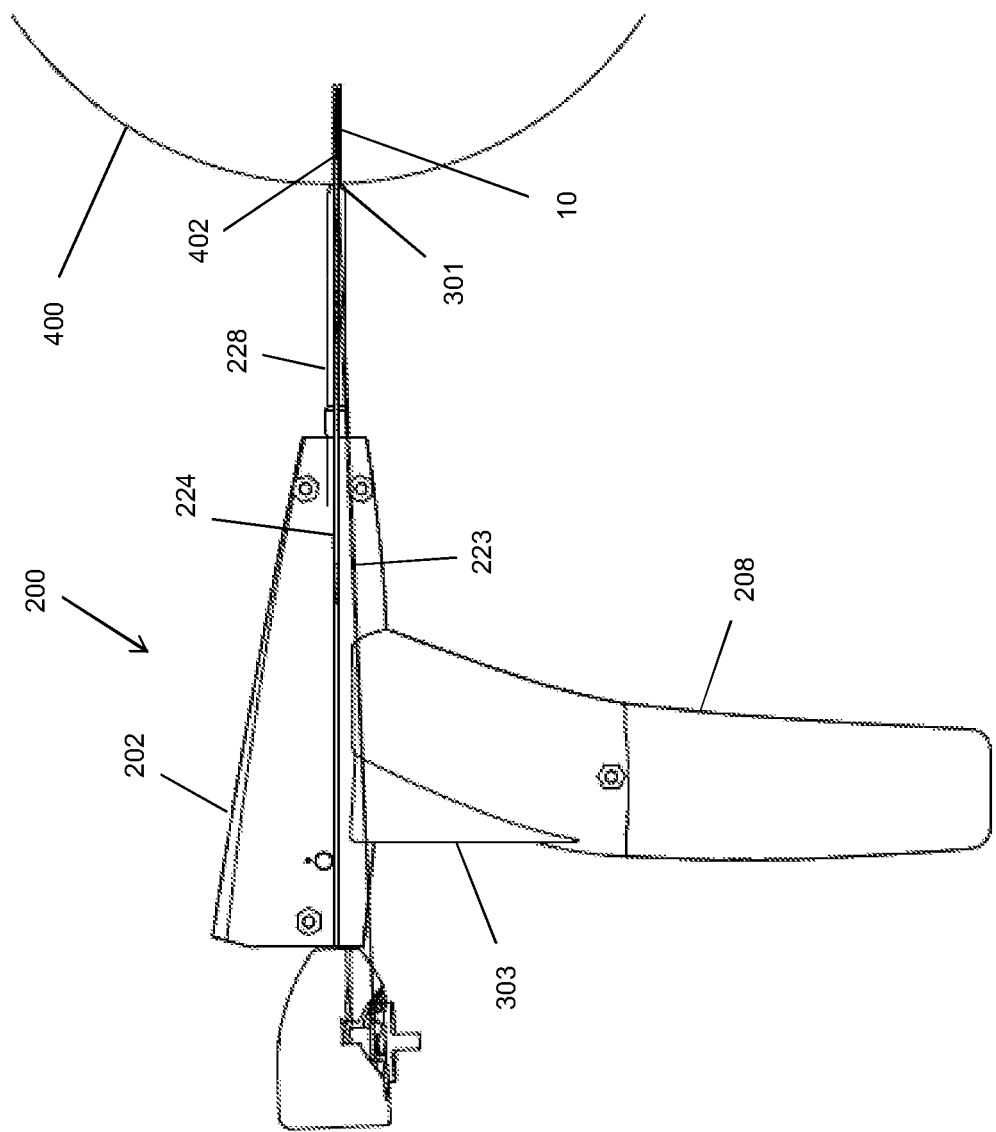
FIG. 12 is an assembled side view schematic representation of a multi-barrel drill guide in use according to an embodiment.

Turning to FIG. 9, in a first step while holding handle 208, a user/medical practitioner positions the teeth 301 against bone 400 to obtain a steady grip of the teeth 301 against the bone 400. Turning to FIG. 10, in a second step, the user distally advances the drill bit 216 to form a pilot hole 402 as shown in FIG. 11. After the pilot hole 402 is formed, in a third step, drill bit 216 is removed from the multi-barrel drill guide 200. Turning to FIG. 12, in a fourth step, anchor driver 218 is distally advanced to deploy anchor 10 into pilot hole 402.

Figure 13:
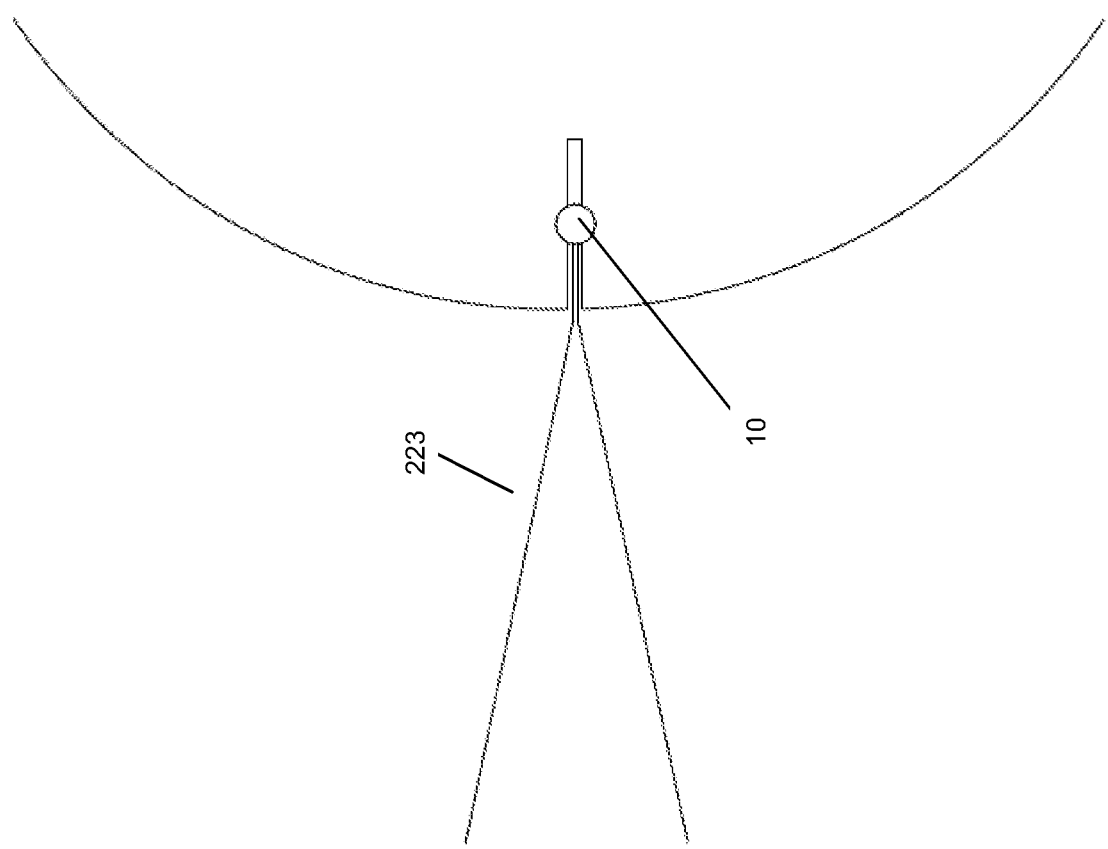
FIG. 13 is a side view schematic representation of a deployed suture anchor deployed by a multi-barrel drill guide according to an embodiment.

After the anchor has been inserted, the suture 223 is pulled from the slot/slit 224 (which is positioned through the outside surface of the elongated body 202). Prior to deployment, the suture 223 is partially positioned through the slot/slit 224 on the side of the main body 202, and into the first channel 210 at the distal end of the channel with the driver 218 and connected to suture anchor 10. The slot 120 extends through the elongated body 202 into the first channel 210 from a distal portion of the first channel to the distal end of the guide 206, and the proximal portion of the slot does not extend into the first channel so the suture 223 won't interfere with the movement of the driver 218 in the first channel 210. After the suture 223 is pulled and removed from the slot/slit 224, the multi-barrel drill guide 200 can be removed from the drill/deployment site (as shown in FIG. 13), and the medical practitioner can finalize the insertion/deployment of the suture anchor 10 (as should be understood by those of skill in the art in conjunction with a review of this disclosure).

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A method of drilling a pilot hole and inserting a suture anchor, the method comprising the steps of:
    providing a multi-barrel drill guide with an elongated body extending along a longitudinal axis having a proximal end and a distal end with a handle extending from the elongated body between the proximal end and the distal end, and an elongated distal guide tube attached to and extending distally from the distal end of the elongated body, wherein there is no movable part on an exterior portion of the elongated body, a first channel extending from the proximal end to the distal end, a second channel extending from the proximal end to the distal end at an angle relative to the first channel, and a convergence area at the distal end where the first channel and the second channel intersect;
    inserting a suture anchor into the first channel and a drill bit into the second channel;
    positioning the distal end of the distal guide tube against a bone;
    extending the drill bit through the convergence area and the distal guide tube; and
    drilling a pilot hole into the bone with the drill bit.

2. The method of claim 1, further comprising the steps of:
retracting the drill bit past a proximal end of the convergence area; and
extending an anchor driver through the first channel and the convergence area.

3. The method of claim 2, further comprising the step of implanting the suture anchor into the pilot hole.

4. The method of claim 3, further comprising the steps of:
pulling a length of suture connected to the suture anchor through a slit in the exterior of the elongated body that extends into the first channel; and
removing the drill guide from the bone.

5. The method of claim 1, wherein the drill guide further comprises a malleting section extending proximally from the handle and a plurality of teeth on the distal end of the elongated body.

6. The method of claim 5, wherein the step of positioning the distal end of the drill guide against the bone further comprises the step of striking the malleting section such that the plurality of teeth grip with the bone.

7. The method of claim 2, further comprising the step of disengaging a locking mechanism from the anchor driver such that the anchor driver can freely move through the first channel.

\* \* \* \* \*